United States Patent [19]

Rudershausen

[11] Patent Number: 5,146,020
[45] Date of Patent: Sep. 8, 1992

[54] DISPROPORTIONATION OF SELECTED CHLOROFLUOROMETHANES

[75] Inventor: Charles G. Rudershausen, Kennett Square, Pa.

[73] Assignee: E. I. du Pont de Nemours and Company, Wilmington, Del.

[21] Appl. No.: 564,690

[22] Filed: Aug. 8, 1990

Related U.S. Application Data

[63] Continuation of Ser. No. 432,314, Nov. 3, 1989, abandoned, which is a continuation of Ser. No. 211,103, Jun. 17, 1988, abandoned, which is a continuation of Ser. No. 85,256, Aug. 11, 1987, abandoned, which is a continuation of Ser. No. 841,949, Mar. 20, 1986, abandoned.

[51] Int. Cl.$^5$ .................. C07C 17/10; C07C 17/20; C07C 19/08; C07C 17/24
[52] U.S. Cl. .................................. 570/163; 570/260
[58] Field of Search ........................................ 570/163

[56] References Cited

U.S. PATENT DOCUMENTS

| 3,087,974 | 4/1963 | Hauptschein et al. | 570/163 |
| 3,087,975 | 4/1963 | Hauptschern et al. | 570/163 |
| 3,087,976 | 4/1963 | Hauptschein et al. | 260/653 |
| 3,138,559 | 6/1964 | Hauptschein et al. | 252/442 |
| 3,651,156 | 3/1972 | Scherer et al. | 570/163 |
| 3,793,229 | 2/1974 | Groppelli et al. | 252/442 |
| 4,192,022 | 3/1980 | Sweeney et al. | 570/163 |

FOREIGN PATENT DOCUMENTS

306566 3/1989 European Pat. Off. ............ 570/163
60-6928 12/1982 Japan .

*Primary Examiner*—J. E. Evans
*Attorney, Agent, or Firm*—James E. Shipley; Robert B. Stevenson; Michael K. Boyer

[57] ABSTRACT

Trifluoromethane or monochlorodifluoromethane and carbon tetrachloride are converted to trichloromonofluoromethane, dichlorodifluoromethane and chloroform using a catalyst of activated aluminum and magnesium oxides.

5 Claims, No Drawings

DISPROPORTIONATION OF SELECTED CHLOROFLUOROMETHANES

This application is a continuation of application Ser. No. 07/432.314 filed Nov. 3, 1989, which in turn is a continuation of application Ser. No. 07/211,103 filed Jun. 17, 1988, which in turn is a continuation of application Ser. No. 07/085,256 filed Aug. 11, 1987, which in turn is a continuation of application Ser. No. 06/841,949 filed Mar. 20, 1986, all now abandoned.

BACKGROUND OF THE INVENTION

This invention relates to a vapor phase process for the disproportionation and rearrangement of chlorofluoromethanes with carbon tetrachloride to yield trichloromonofluoromethane, dichlorodifluoromethane, and chloroform, using an activated alumina and magnesia catalyst.

Generally, fluorinated alkanes are produced commercially by reacting hydrogen fluoride with chloroalkanes in the presence of a catalyst: Daudt et al., U.S. Pat. Nos. 2,005,705 and 2,005,708. The fluorination reaction may be represented by the following equation using chloroform as the illustrative haloalkane:

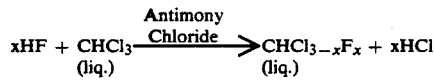

wherein x is 1 to 3. A mixture of products, dichloromonofluoromethane ($CHCl_2F$), monochlorodifluoromethane ($CHClF_2$), and trifluoromethane ($CHF_3$), is usually obtained from this reaction. The amount of each reactant which is produced depends on the process feed ratios and the reaction conditions. However, it is not generally possible to completely avoid the production of undesirable products through control of process parameters. For example, the production of $CHF_3$ frequently exceeds demand and the fluorine values in the $CHF_3$ are usually wasted because no economical process is known for their recovery.

JP Patent No. 60-6928 describes a catalyst for disproportionation of fluorine-containing halocarbons. The catalyst consists of chromium oxide, magnesium oxide, and aluminum oxide and contains mostly aluminum oxide based on the weight of total oxides. U.S. Pat. Nos. 3,087,976 and 3,793,229 disclose the use of an alumina catalyst activated by reacting with hydrogen fluoride and a lower fluorocarbon, respectively. Use of these known catalysts to disproportionate trifluoromethane led to the formation of monochlorotrifluoromethane, an even less desirable product.

It is therefore an object of the present invention to recover fluorine values by selective disproportionation of chlorofluoromethanes to obtain the commercially significant products, trichloromonofluoromethane, dichlorodifluoromethane, and chloroform. The chloroform which is also produced from this reaction can be used for other purposes, e.g., recycled to the primary fluorination reaction above.

SUMMARY OF THE INVENTION

In accordance with the present invention, there is provided a process for producing trichloromonofluoromethane, dichlorodifluoromethane and chloroform comprising the steps of:

(a) reacting, in the vapor phase, trifluoromethane or monochlorodifluoromethane and carbon tetrachloride in the presence of an effective amount of a catalyst consisting essentially of activated aluminum and magnesium oxides at a temperature of about 150° to 350° C., a pressure of about 0.1 to 25 atmospheres, a molar feed ratio of chlorofluorocarbon to carbon tetrachloride of about 0.1 to 10.0 and a contact time of about 0.2 to 20 seconds to produce trichloromono-, dichlorodifluoromethane and chloroform as the primary reaction products, and (b) separating the trichloromonofluoromethane, difluorodichloromethane and chloroform from the reaction product of step (a).

The process of this invention provides excellent disproportionation activity and selectivity at moderate process conditions. In addition, fluorine values which are usually wasted are effectively used to produce commercially useful fluorocarbons, e.g., refrigerants.

DETAILED DESCRIPTION OF THE INVENTION

The catalyst of this invention can be prepared by different methods and can have a wide range of proportions of magnesium and aluminum oxides, but aluminum oxide alone or magnesium oxide alone is inadequate. A catalyst composition which varies from 1-99% aluminum oxide and 99-1% magnesium oxide is operable; a catalyst composition which varies from 97-3% aluminum oxide and 3-97% magnesium oxide is preferred; a catalyst composition which varies from 90-10% aluminum oxide and 10-90% magnesium oxide is more particularly preferred. The most preferred catalyst composition varies from 60-30% aluminum oxide and 40-70% magnesium oxide.

One embodiment of the invention involves preparation of the catalyst by simultaneously combining aqueous $Al_2O_3.9H_2O$, $MgNO_3.6H_2O$ and $NH_4OH$. The precipitate is water-washed, dried and calcined to yield a catalyst containing magnesium and aluminum oxides. After calcination, the catalyst can be crushed to a preferred particle size, such as 10-20 mesh.

Other methods which can be used to prepare the catalyst of this invention are well known to those skilled in the art of catalyst manufacture and include but are not limited to techniques such as physically mixing aluminum oxide and magnesium oxide together and thereafter pelletizing this mixture and using the pellets as formed or crushed to a desired particle size. Another method of preparation is to extrude a suitable slurry containing the desired aluminum and magnesium and thereafter calcine and crush to reduce particle size, if desired. Also, an inert surface could be impregnated with an aqueous solution of aluminum and magnesium nitrates and thereafter dry the surface and calcine to remove the nitrates so as to leave aluminum and magnesium oxides impregnated in the surface.

The catalyst must be activated before use. Activation can be accomplished by contacting the catalyst with a vaporized fluorine-containing compound. One particularly desirable method of activating the catalyst involves treating it in the reactor to be used for disporportionation with a gaseous stream of nitrogen containing anhydrous hydrofluoric acid. The gaseous stream can be passed over the catalyst for several hours while the temperature and hydrofluoric acid concentration are increased. Nitrogen dilutes the hydrofluoric acid to minimize the exothermic temperature excursion. After activation, the catalyst is cooled and can be left in the reactor equipped with feed parts by which trifluoromethane or monochlorodifluoromethane and carbon tetrachloride can be introduced into the reactor.

Trifluoromethane or monochlorodifluoromethane and carbon tetrachloride are thereafter fed to a reactor containing an effective amount of the activated catalyst where the disproportionation reaction occurs using effective process conditions. By effective amount of the activated catalyst and effective process conditions is meant amounts of activated catalyst and process conditions which form trichloromonofluoromethane, dichlorofluoromethane and chloroform as primary reaction products.

A variety of molar feed ratios of trifluoromethane or monochlorodifluoromethane to carbon tetrachloride, catalyst contact times, temperatures and pressures can be used. The operable ranges of process conditions include temperatures of about 150°-350° C., molar feed ratios of about 0.1-10, and catalyst contact times of about 0.2 to 20 seconds. It has been found that temperatures higher than about 350° C. result in impractical catalyst deactivation. In addition, the molar feed ratios may be varied depending on the desired degree of conversion of the respective starting materials at a given temperature and catalyst contact time. Operating pressure for the process need not be limited to one atmosphere. To facilitate downstream separations and to reduce refrigeration loads required to separate the reactants using distillation, the reactor may preferably be operated at substantially higher pressures. In certain other cases, it may be commercially advantageous to operate the reactor at subsatmospheric pressure. An operable range of process pressures is 0.1 to 25 atmospheres.

The preferred ranges of process parameters for this invention are temperatures of about 200° to 300° C., catalyst contact times of about 1 to 5 seconds, molar feed ratios of the raw materials of about 0.5 to 2.0, and about 1 to 5 atmospheres pressure. A preferred set of process parameters for this invention is a temperature of about 250° C., a catalyst contact time of about 3 seconds, a molar feed ratio of the raw materials of about 1.5, and about atmospheric pressure.

The process of this invention may use any appropriate reactor. A shell and tube type reactor is particularly desirable in which the catalyst is loaded into the tubes from which the heat of reaction is removed by transfer to hot water to produce steam. The steam pressure can be regulated to correspond to the reaction temperature desired in the catalyst bed.

Continuous or batch distillation can be used to separate unreacted feed components and the products of the reaction which are primarily trichloromonofluoromethane, dichlorodifluoromethane, and chloroform.

EXAMPLES

The following examples illustrate particular aspects of the present invention.

EXAMPLE 1

A coprecipitated catalyst was prepared by first adding 110 grams of $Al(NO_3)_3.9H_2O$ and 110 grams of $Mg(NO_3)_2.6H_2O$ to 250 ml. of distilled water. A second solution of 200 ml. of reagent grade ammonium hydroxide (28%) in 800 ml. of distilled water was also prepared. Both solutions were heated to 60°-80° C. and each poured into its respective separating funnel. The contents of each funnel were admitted to 1 liter of distilled water, heated to 80° C. while contained in a beaker and continuously stirred. The discharge points were placed subsurface and near the stirring bar to assure uniformity during precipitation. A pH meter was used with probe set to hold the pH at about 8.9 during the half hour taken to control the discharge of the entire contents of the two funnels. The precipitate was vacuum-filtered and then displacement washed with 2 liters of distilled water at 80° C.

The filter cake was dewatered on the vacuum filter, further dried in a vacuum oven at 170° C. for 16 hours, and finally calcined at 500° C. for five hours to produce 31.5 grams of hard particulate. This was crushed and screened through 10-mesh screen. The portion retained on a 20-mesh screen was used for catalyst testing. (The finished catalyst contained the metals in the weight ratio of Al/Mg of approximately 43/57.)

Five cubic centimeters (cc) of this catalyst was placed in a 7 cc Inconel tube (reactor) which was placed in a fluidized and heated sand bath. The catalyst was activated by treating with a gaseous stream of nitrogen containing 25% anhydrous HF at a total flow rate of 125 ml (measured at room temperature and pressure) beginning at a reactor temperature of 168° C. Over a period of three hours, the gaseous stream was gradually enriched to 75/25 $HF/N_2$ while the temperature was raised to 300° C. The catalyst was then cooled to 200° C. with flowing nitrogen and reduced electrical heating of the sand bath.

EXAMPLE 2

Same as Example 1, but only 5 grams of $Mg(NO_3)_2.6H_2O$ were used which yielded 11.4 grams calcined catalyst containing 94/6 weight percent of Al/Mg.

EXAMPLE 3

Same as Example 1, but only 5 grams of $Al(NO_3)_3.9H_2O$ were used which yielded 16.1 grams calcined catalyst containing 3/97 weight percent of Al/Mg.

EXAMPLE 4

The activated catalyst of Example 1 was left in the reactor already equipped with feed parts by which $CHF_3$ was fed from a cylinder through a mass flow meter at 28 cc/min (1 atm., 20° C.). Carbon tetrachloride was fed from a positive displacement pump through a vaporizer and cofed as a vapor at the same volume, 28 cc/min. With the catalyst (reactor) now heated to 250° C., retention time in the catalyst bed was a nominal three seconds. The reactor was operated substantially at 1 atmosphere. Product (effluent) was analyzed with a gas chromatograph (flame ionization) as shown in the table.

EXAMPLES 5, 6 and 7

Using the catalyst of Example 1, the parameters of the process described in Example 4 were varied over a range of temperatures, molar feed ratios, retention times and pressures. The results are shown in the table. Excellent activity and selectivity is evident. Conversion to the unwanted by-product, $CClF_3$, remained at less than 1 mole percent of the halocarbon effluent.

EXAMPLE 8

Using the catalyst of Example 1 and the process of Example 4 but with a reaction temperature of 200° C. and a molar feed ratio of 1:1, monochlorodifluoromethane was used as the fluorochlorocarbon feed instead of trifluoromethane, again showing excellent activity and selectivity. The results are shown in the table.

The following examples use catalysts as described in each example and the process as described in Example 4 with process conditions for temperature, molar feed ratio, and catalyst contact time adjusted as shown in the table.

EXAMPLES 9 and 10

Examples 9 and 10 used the catalysts of Examples 2 and 3 respectively. The results are shown in the table. Again, good selectivity and activity are evident for catalysts containing both aluminum and magnesium.

EXAMPLE 11

A catalyst was prepared as described in Example 1 but 10 grams of $Cr(NO_3)_3 \cdot 9H_2O$ were included in the starting solution prior to precipitation; the final catalyst contained Al/Mg/Cr in the percentage weight ratio of 40/53/7. The results are shown in the table as Example 11. The addition of the chromium did not have a serious detrimental effect on the performance of the catalyst.

and chloroform as the primary reaction products, and (b) separating the trichloromonofluoromethane, difluorodichloromethane and chloroform from the reaction product of step (a).

2. The process of claim 1 wherein the catalyst contains at least about 3 percent each of aluminum or magnesium as a weight percentage of total aluminum and magnesium.

3. The process of claim 1 wherein the catalyst contains from 90 to 10 weight percent aluminum oxide and 10 to 90 weight percent magnesium oxide.

4. The process of claim 1 wherein the catalyst contains from 60 to 30 weight percent aluminum oxide and 40 to 70 weight percent magnesium oxide.

5. A process for producing trichloromonofluoromethane, dichlorodifluoromethane and chloroform comprising the steps of:

(a) reacting, in the vapor phase, trifluoromethane or monochlorodifluoromethane and carbon tetrachloride in the presence of an effective amount of a catalyst consisting essentially of activated aluminum and magnesium oxides in which the amount of

| | | | DISPROPORTIONATION OF $CHF_3$ WITH $CCl_4$ AT 1 ATMOSPHERE | | | | | | | |
|---|---|---|---|---|---|---|---|---|---|---|
| | Temp | Mole Feed Ratio | CT | Mole % of Effluent Halocarbons | | | | | | |
| Example | °C. | $CHF_3/CCl_4$ | Sec | $CCl_4$ | $CCl_3F$ | $CCl_2F_2$ | $CHF_3$ | $CClF_3$ | $CHCl_3$ | $CHCl_2F$ | $CHClF_2$ |
| 4 | 250 | 1/1 | 3 | 14.5 | 8.4 | 24.6 | 25.4 | 0.2 | 24.4 | 1.1 | 1.2 |
| 5 | 200 | 0.5/1 | 5 | 42.5 | 13.3 | 7.3 | 22.2 | 0 | 14.0 | 0 | 0 |
| 6 | 300 | 0.5/1 | 5 | 27.7 | 9.5 | 26.9 | 6.6 | 0.4 | 27.8 | 0.8 | 0.5 |
| 7 | 225 | 0.5/1 | 3 | 36.3 | 11.3 | 18.0 | 17.2 | 0.3 | 16.3 | 0.3 | 0.3 |
| 8 | 200 | 1/1* | 3 | 14.7 | 4.6 | 26.2 | 9.0 | 0.5 | 43.9 | 0.8 | 0.5 |
| 9 | 150 | 1/1 | 3 | ND | 4.0 | 37.0 | ND | 3.0 | 20.0 | ND | ND |
| 10 | 200 | 1/1 | 3 | 17.0 | 16.0 | 10.0 | 35.0 | 0.04 | 15.0 | 0.5 | 0.8 |
| 11 | 200 | 1/1 | 3 | 11.0 | 10.0 | 28.0 | 28.0 | 1.0 | 21.0 | 0.7 | 0.9 |

*1/1 $CHClF_2/CCl_4$

I claim:

1. A process for producing trichloromonofluoromethane, dichlorodifluoromethane and chloroform comprising the steps of:

(a) reacting, in the vapor phase, trifluoromethane or monochlorodifluoromethane and carbon tetrachloride in the presence of an effective amount of a catalyst consisting essentially of activated aluminum and magnesium oxides at a temperature of about 150° to 350° C., a pressure of about 0.1 to 25 atmospheres, a molar feed ratio of chlorofluorocarbon to carbon tetrachloride of about 0.1 to 10.0 and a contact time of about 0.2 to 20 seconds to produce trichloromono-, dichlorodifluoromethane magnesium in the catalyst is at least 5 percent by weight of the catalyst's total metals content at a temperature of about 150° to 350° C., a pressure of about 0.1 to 25 atmospheres, a molar feed ratio of chlorofluorocarbon to carbon tetrachloride of about 0.1 to 10.0 and a contact time of about 0.2 to 20 seconds to produce trichloromonofluoromethane, dichlorodifluoromethane and chloroform as the primary reaction products, and (b) separating the trichloromonofluoromethane, difluorodichloromethane and chloroform from the reaction product of step (a).

* * * * *